United States Patent [19]

Pettit

[11] Patent Number: 4,997,817
[45] Date of Patent: Mar. 5, 1991

[54] PHYLLANTHOSTATIN A

[75] Inventor: George R. Pettit, Scottsdale, Ariz.

[73] Assignee: Arizona Board of Reagents, Tempe, Ariz.

[21] Appl. No.: 467,683

[22] Filed: Jan. 19, 1990

[51] Int. Cl.$^5$ .................... A61K 31/71; C07H 7/06; C07H 13/00
[52] U.S. Cl. ..................................... 514/25; 536/4.1; 536/18.1
[58] Field of Search ................... 536/4.1, 18.1; 514/25

[56] References Cited

U.S. PATENT DOCUMENTS 4,388,457 6/1983 Pettit .................. 536/18.1

Primary Examiner—Johnnie R. Brown
Assistant Examiner—Elli Peselev
Attorney, Agent, or Firm—Richard R. Mybeck

[57] ABSTRACT

An unusual cytostatic (PS ED$_{50}$ 4 ug/ml) lignan ester has been isolated from the Central American tree *Phyllanthus acuminatus* and is herein designated Phyllanthostatin A. Separation of a methanol extract of the root by size exclusion chromatography, high speed countercurrent distribution and semi-preparative hplc afforded glycoside in 0.007% yield. In solution, phyllanthostatin A was slowly transformed into justicidin-B. The structure of the lignan glycoside, determined by hrfabms and 2D nmr spectroscopy, is:

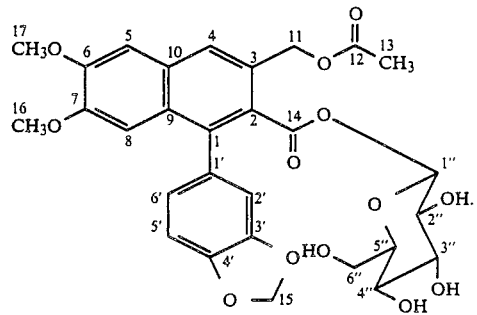

4 Claims, No Drawings

PHYLLANTHOSTATIN A

The work described herein was funded in part under Grant CA - 30311-01-03 awarded by The National Cancer Institute and Contract NO1-CM-97262 with the Division of Cancer Treatment, NCI, National Institute of Health.

INTRODUCTION

The present invention relates to the isolation and structural elucidation of a new lignan glycoside, herein denominated "phyllanthostatin A", which is obtained from the Central American tree *Phyllanthus acuminatus*. The structure of this lignan glycoside was determined by hrfabms and 2D NMR spectroscopy. The substance demonstrated cystostatic properties (PS $ED_{50}=4$ $\mu$g/ml) and has the general structural formula:

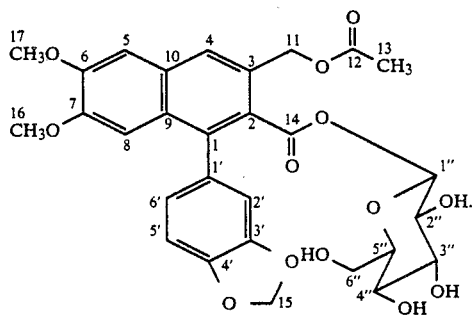

BACKGROUND OF THE INVENTION

The potentially important phyllanthostatin-type antineoplastic glycosides were first discovered by George R. Pettit (Cancer Research Institute, Arizona State University, Tempe, Ariz.) during previous investigations of the Costa Rican tree *Phyllanthus acuminatus* Vahl (Euphorbiaceae) as reported in *J. Org. Chem.*, 49, 4258 (1984). Presently, the orthoacid equilibrium product phyllanthostatin 1 phyllanthoside [see: *J. Org. Chem..* 50, 5060 (1985)] is undergoing preclinical development by the U.S. National Cancer Institute and total synthesis of phyllanthoside and the aglycone phyllanthocin have been completed. Because of the easily promoted orthoacid rearrangement uncovered during structural elucidation of the phyllanthostatins, it became necessary to reevaluate their abundance, and possibly detect new members of the series, in relatively fresh *P. acuminatus* roots using the high performance liquid chromatographic analyses photodiode array detector reported in *Chromatographia*, 15, 419(1982) and *J. Chromatogr.*, 283, 137(1984) at an early stage of separation.

During this ongoing research, a previously unknown lignan glycoside was discovered which is herein denominated "phyllanthostatin A" and which, was found to inhibit growth of the PS leukemia cells in vitro at a concentration of $ED_{50}=4$ $\mu$g/ml.

BRIEF SUMMARY OF THE INVENTION

The present invention relates to the discovery of a new lignan glycoside substance having cytostatic properties, herein denominated "Phyllanthostatin A", which is extracted from the Central American tree *Phyllanthus acuminatus*. The substance, when measured by the generally accepted protocol for P388 murine/lymphocytic/leukemia in use at the United States National Cancer Institute, demonstrated a PS $ED_{50}$ of 4 $\mu$g/ml.

The principal object of the present invention is to isolate and identify a new natural substance which can be utilized in the treatment and management of those neoplastic diseases which are characterized by uncontrolled cell growth and have an established correlation to the NCI protocol for P388 murine lymphoctyic leukemia.

Another object of the present invention is to elucidate unequivocally the structure of a newly discovered lignan glycoside denominated "phyllanthostatin A" so as to provide a readily discernible target for the direction of future synthetic endeavors.

These and still further objects as shall hereinafter appear are fulfilled by the present invention in a remarkably unexpected fashion as will be readily discerned by a careful consideration of the embodiments thereof especially when read in conjunction with the accompanying drawings.

BRIEF DESCRIPTION OF THE DRAWINGS

In the drawings.

FIG. 1 is a downfield segment of the $^1$H,$^{13}$C COSY spectrum of phyllanthostatin A in CDCL$_3$; and FIG. 2 is a partial $^1$H nmr spectra of phyllanthostatin A (a-e) and justicidin (f) in DMSO-d$_6$ at various temperatures.

DESCRIPTION OF PREFERRED EMBODIMENTS

Roots of *P. acuminatus* (345 g) were extracted successively with hexane, CH$_2$Cl$_2$, and MeOH. The methanol extract was analyzed by hplc with photodiode array detection (hplc-uv/vis). The crude extract chromatogram displayed the more abundant phyllanthostatin-type glycosides such as phyllanthoside [$\lambda$max=277 nm] and a previously unknown minor constituent with uv absorption maxima at 248 and 288 nm. Hplc-uv/vis and cell growth inhibition against the P388 murine lymphocytic leukemia (in vitro PS system) were used to guide the isolation of the lignan. The methanol extract (22 g) was separated by size exclusion chromatography (SEPHADEX$^R$LH-20; MeOH) and a phyllanthostatin A rich fraction was further separated by high-speed countercurrent distribution with a multilayer coil planet centrifuge. Aliguots of 2 g (or less) of the active fraction were separated using the system n-hexane-CH$_2$Cl$_2$-MeOH-H$_2$O (1:5:4:3) where the lower phase was employed as the mobile solvent. The HSCCD separations were completed in less than three hours and led to nearly pure phyllanthostatin A. These fractions were combined and further separated by reversed-phase semi-preparative hplc (50% aq. MeOH to MeOH) yielding 25 mg of phyllanthostatin A (0.007% yield). Additional phyllanthostatin A was subsequently isolated from fractions placed aside during an earlier large-scale isolation of other substances from the roots of *P. Acuminatus*.

The structural elucidation of phyllanthostatin A was not readily accomplished because it was unstable in solution and split or doubled signals appeared in its nmr spectrum. However, hrfabms enabled the molecular formula to be determined as $C_{29}H_{30}O_{13}$. The uv spectrum with absorption maxima at 248 and 288 nm was similar to that recorded for justicidin B previously found in *P. acuminatus*. However, the ir spectrum contained an ester band at 1738 cm$^{-1}$ and the lactone absorption typical of lignan 2, was absent.

The fabms spectrum of phyllanthostatin A showed a molecular ion at m/z 586 [M]+ and fragmentation pattern with ions at m/z 424 and 365. The latter were explained by elimination of glucose [M-162]+ and acetate-water [(M+H)-162-60]+ respectively from the parent species. The ion at m/z 424 also indicated that the acetyl group ($^1$H nmr: δ2.09 ppm) was not bonded to the glucose unit. Such an interpretation was further supported by the fabms spectra of the peracetate and perpropionate derivatives of phyllanthostatin A. Both showed the ion at m/z 424 and suggested that glycoside was a justicidin B precursor bearing groups derived from acetic acid and D-glucose.

Acid hydrolysis of glycoside afforded a chloroform soluble degradation product identified as justicidin B by comparison with an authentic sample (cotlc, mp, uv, ir, eims, $^1$H nmr). Justicidin B was also detected in MeOH solutions of glycoside stored at room temperature for two days. The sugar moiety obtained by acid hydrolysis was identified as D-glucose by peracetylation and comparison (ir, eims, $^1$H nmr) with authentic D-glucose pentaacetate. The glucose β-configuration was deduced from the $^1$H-nmr doublet at δ5.34 and 5.30 ppm (doubled signal, 2 x J =8.0 Hz; DMSO-d$_6$) and from the doublet at δ5.58 and 5.55 ppm (doubled signal, 2 x J =8.0 Hz; CDCl$_3$). In addition, the $^{13}$C nmr chemical shifts corresponded to those reported for β-D-glucose esters and the shift of the anomeric carbon ( δ=94.37 ppm) indicated an ester linkage through the C-1" hydroxyl.

The nmr spectra of glycoside was recorded in three different solvents (CDCl$_3$, CD$_3$OD, and DMSO-d$_6$) and at different sample concentrations, and all showed several split or doubled resonances, (cf, FIG. 1,2 and Tables 1–3, shown below) including those assigned to ring-C carbons and protons. These observations are illustrated by the downfield region of the 2D-$^1$H,$^{13}$C-COSY spectrum of phyllanthostatin A shown above. Connectivities between carbons C-4, C-5 and their attached protons were deduced by the single correlation peaks at 126.92/7.54 and 106.37/7.06 ppm, respectively. But the correlation peaks of carbons C-2', C-5', C-6', C-8 and their corresponding protons were all doubled. Results of 2D homo- and heteronuclear correlation experiments as well as nuclear Overhauser difference spectroscopy (NOEDS) were in agreement with the structure shown below and excluded mixtures of possible isomers. The most useful nOe's were observed when protons H-4, H-5, H-8, H-11, H-16, and H-17 were irradiated and led to establishing correlations between H-4 and H-5, H-4 and H-11, H-5 and H-17, H-8 and H-16.

The structure referred to above is as follows:

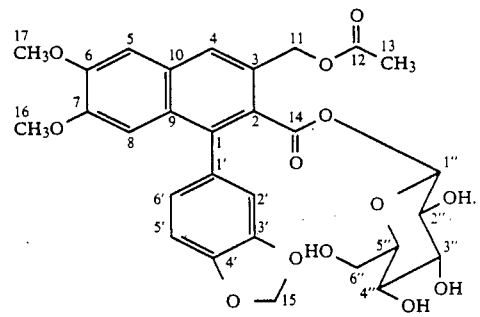

The deductions reported above were further confirmed by the $^{13}$C-nmr spectrum which showed resonances corresponding to carbons 1,2,3,8,9,1'-6'all split by about 0.1–0.2 ppm. Signals of the remaining carbons appeared as sharp single lines. These observations are explained by hindered rotation around the C-1/C-1' axis, resulting in conformational isomers. In order to provide evidence for or disprove this hypotheses, the $^1$H nmr spectra of the glycoside (shown above) were recorded in DMSO-d$_6$ at different temperatures. Table 1 summarizes the chemical shifts observed at 25, 65, 105, 135, and 145° C. FIG. 2 shows that part of the spectra representing C-ring protons and the overlapping H-8 proton. Room temperature (FIG. 2a) led to a complex coupling pattern that became more easily interpretable when the spectrum was recorded at 65° C. (FIG. 2b). Signals due to H-2', H-5' and H-6' broadened and disappeared when the temperature was raised (FIG. 2c). At higher temperatures (FIGS. 2d,e) phyllanthostatin-A gradually decomposed and signals appeared attributable to justicidin B. By subtracting these signals (FIG. 2f) from the spectrum in FIG. 2e, it became possible to assign the doublets δ6.91 (J=8.0 Hz, overlapped with the H-8 singlet) and 6.81 (J=1.5 Hz), as well as the doublet of doublets at 6.77 (J=1.5 Hz, J=8.0 Hz) to the C-ring protons H-5', H-2' and H-6', respectively. Other protons (not shown in FIG. 2) also appeared as single resonances at higher temperatures. These experiments served to prove that the diester was a single compound and the double signals were due to conformational isomers in solution.

Assignment of the ring-A, -B and -C carbons and protons was achieved by 2D heteronuclear correlation methods and the conclusions are summarized in Table 3. Quaternary carbon resonances were established by means of long-range coupling (mainly over three bonds) observed in a 2D-$^1$H, $^{13}$C-COLOC experiment, optimized for J=5 Hz. Based on this experiment, the signal at 172.92 was assigned to the C-12 carbonyl showing a two bond coupling to the H-13 protons. The second carbonyl appeared at δ167.42 ppm and was characterized by a small W path coupling with H-4 and by pronounced correlation peak with the anomeric glucose proton (three bond coupling). In turn this confirmed the glucose ester linkage and allowed assignment of the structure shown to phyllanthostatin A.

Phyllanthostatin A was found to inhibit growth of the PS388 leukemia cells in vitro at a concentration of ED$_{50}$=4 μμg/ml. In vivo studies are currently in progress.

To further assist in the understanding of the present invention and not by way of limitation, the following examples are presented.

EXAMPLE I

General Procedures

All solvents employed were redistilled. Absorption column chromatography was performed with silica gel 60 (70-230 mesh, E. Merck, Darmstadt, Germany) Reversed-phase chromatography was accomplished with RP-8 Lobar columns (size B, 40-63 um, from E. Merck) and size exclusion chromatography with SEPHADEX LH-20 (particle size: 25-100 m supplied by Pharmacia Fine Chemicals, Uppsala, Sweden) Thin layer chromatography was carried out with silica gel GHLF Uniplates (Analtech Inc.) and with RP-8 precoated plates (layer thickness: 0.25 mm) from E. Merck. The tlc plates were examined under uv light and developed with anisaldehyde spray reagent.

High-speed countercurrent distribution (HSCCD) was carried out with an Ito Multilayer Coil Extractor-Separator (P.C. Inc., Potomac, Md., using 2.6 mm I.D. tubing), a FMI Lab Pump, a Linear recorder, and Gilson Model Holochrome uv/vis detector (2.5 mm/3.2 $\mu$cell) and Micro Fractionator. Analytical hplc with photodiode array detection (hplc-uv/vis) was accomplished with a ULTREMEX RP-8 column (100×4.6 mm I.D., 3 $\mu$m, PHENOMENEX, Rancho Palos Verde, Calif.) at a flow rate of 1 ml/min. and a linear gradient of aq. $CH_3CN$ (20% to 70% in 15 min). The mobile phase was delivered by two Gilson Model 302 pumps using an Apple IIe programmer. Chromatograms and spectra were recorded with a HP 1040A photodiode array detector and a HP 79994 work station (Hewlett-Packard). Semi-preparative hplc was performed with a Prepex RP-8 column (250×10 mm I.D., 5-20 $\mu$m, Phenomenex) with aq. $CH_3OH$ (50% to 100% in 1 hr.) at a flow rate of 2 ml/min. Melting points are uncorrected and were determined on a Kofler-type hot-stage apparatus. Optical rotations were measured using a Perkin-Elmer Model 241 Automatic Polarimeter. Uv were recorded by employing a Hewlett-Packard Model 8450A uv/vis spectrophotometer and ir spectra with a Nicolet ft-ir Model MX-1 instrument Nmr spectra were measured using a Bruker AM-400 instrument and are recorded in ppm downfield to TMS. The $^{13}C$ nmr multiplicities were determined with APT experiments based on an average coupling constant of 135 Hz. Both 2D homo- and heteronuclear shift correlated spectra were recorded using standard pulse sequences. Eims spectra were obtained using a Varian MAT 312 spectrometer. Fabms spectra were recorded with a MS-50 instrument at the NSF Regional Facility, University of Nebraska, Lincoln, Nebr.

EXAMPLE II

Plant Material, Extraction and Countercurrent Distribution

Roots of *P. acuminatus* were collected in Cost Rica in 1986. A voucher specimen (B680433) is maintained at the Cancer Research Institute at Arizona State University. The air dried roots (345 g) were powdered and extracted (at room temp.) successively with n-hexane, $CH_2Cl_2$ and $CH_3OH$ (3×6 liters each) yielding 0.6, 3.6 and 25.0 g of extracts, respectively. An aliquot of the methanolic extract (22 g, $ED_{50}=15$ $\mu$g/ml) was separated by size exclusion chromatography (SEPHADEX LH-20, 100×10 cm I.D.; $CH_3OH$) and 6 fractions were collected. Fraction 5 (elution vol. 6700-8700 ml: 4174 mg; $ED_{50}=20$ $\mu$g/ml) was separated by HSCCD with the solvent system n-hexane-$CH_2Cl_2$-$CH_3OH$-$H_2O$ (1:4:5:3) Samples ($\leq$2g) were dissolved in about 10 ml of both phases and introduced into the coil through the head-inlet. Elution was conducted through the same inlet at flow rates between 200 and 240 ml/h with the lower (=mobile) phase. Rotation of the coil was at 800 rpm and retention of the stationary phase was usually about 80%. Uv detection was carried out at 254 nm and fractions collected every 2 min.

EXAMPLE III

Isolation of Phyllanthostatin A.

Phyllanthostatin A containing fractions (48 from the HSCCD separation were combined and further purified by semi-preparative hplc affording 25 mg of pure glycoside. In addition, phyllanthostatin A was isolated from a fraction obtained during the large-scale separation of *P. acuminatus*. Phyllanthostatin A was detected by hplc-uv/vis and the corresponding fractions (380 g) were dissolved in 1 liter of $CH_3OH$ and separated by size exclusion chromatography (SEPHADEX LH-20, 100×10 cm I.D.). The Phyllanthostatin A rich fractions were combined (8.5 g, elution vol. 6-7 liters, $ED_{50}=3.1$ $\mu$g/ml) and further separated ($\leq$2 g samples) by HSCCD using n-hexane-$CH_2Cl_2$-$CH_3OH$-$H_2O$ (2:5:4:3) as the solvent system. The organic layer was used as the mobile phase. The combined fractions were finally purified by reversed-phase liquid chromatography (Lobar, size B) with aqueous $CH_3OH$ (60%) as mobile phase, affording 1.06 g ($7\times10^{-5}$% yield) of phyllanthostatin A: amorphous solid; mp 127°-130° C.; tlc on silica gel Rf=0.38, $CH_2Cl_2$-$CH_3OH$ (9:1), Rf=0.25, n-hexane-$CH_2Cl_2$-$CH_3OH$-$H_2O$ (1:4:5:3, lower phase); $[\alpha]D^{26}$+24.5 (c=1.5; $CH_2Cl_2$); hrfabms: m/z 586.1703 $[M]^+$ (calculated for $C_{29}H_{30}O_{13}$: 586.1677, $\Delta$=4.4 ppm), 424 $[M-162]^+$, 365 $[(M+H)-162-50]^+$; $uv_{max}$ 248 (log $\epsilon$=4.72), 288, (4.02) nm; ir $\nu_{max}$ 3525, 2850, 1738, 1507, 1492, 1471, 1433, 1240, 1155, 1060, 1038 cm$^{-1}$; $^1H$-and $^{13}C$-nmr see Tables 1-3 set forth below. NOED spectra were recorded without degasing and the following enhancements (in parentheses; negative values) were observed upon irradiation: H-4 (H-5: 6.2%), H-11: 1.2%, 1.5%), H-5 (H-4: 8.1%; H-17: 8.6%); H-8 (H-16: 6.2%), H-11 (H-4: 2.3%), H-16 (H-8: 11.0%), H-17 (H-5: 9.2%); $^1H,^{13}C$-COSY and $^1H,^{13}C$-COLOC, see Table 3 below.

TABLE 1

| | High field (400 MHz) $^1H$ nmr chemical shifts for phyllanthostatin A and justicidin B from 25-145° C. | | | | | | |
|---|---|---|---|---|---|---|---|
| | phyllanthostatin A | | | | | justicidin B | |
| assignment | 25° C. | 65° C. | 105° C. | 135° C. | 145° C. | 25° C. | 145° C. |
| H-4 | 7.85 s | 7.83 s | 7.81 s | 7.80 s<br>7.90 s$^b$ | 7.79 s<br>7.88 s$^b$ | 7.95 s | 7.88 s |
| H-5 | 7.45 s | 7.41 s | 7.40 s | 7.39 s<br>7.44 s$^b$ | 7.37 s<br>7.43 s$^b$ | 7.52 s | 7.43 s |
| H-8 | 6.92-6.89 | 6.89 s | 6.89 s | 6.90 s<br>7.06 s$^b$ | 6.90 s<br>7.06 s$^b$ | 7.00 s | 7.07 s |

TABLE 1-continued

High field (400 MHz) $^1$H nmr chemical shifts for phyllanthostatin A and justicidin B from 25-145° C.

| assignment | phyllanthostatin A | | | | | justicidin B | |
|---|---|---|---|---|---|---|---|
| | 25° C. | 65° C. | 105° C. | 135° C. | 145° C. | 25° C. | 145° C. |
| H-11 | 5.29-5.14 m | 5.29, 5.26 5.23, 5.19 4 × d(~12) | 5.27, 5.22 2 × d(~12) | 5.28, 5.23 2 × d(~12) 5.39 br s$^b$ | 5.23, 5.28 2 × d(~12) 5.37 s$^b$ | 5.44 s | 5.38 s |
| H-13 | 2.09 s | 2.06 s | 2.06 s | 2.05 s | 2.05 s 1.88 s$^c$ | | |
| | | | | 1.88 s$^c$ | | | |
| H-15 | 6.18-5.98 | 6.18-5.92 | ~6.06 br | 6.03 br m 6.07 s$^b$ | 6.02 br d 6.06 s$^b$ | 6.14 s | 6.06 s |
| H-16 | 3.66 s | 3.66 s | 3.66 s | 3.67 s 3.69 s$^b$ | 3.67 s 3.69 s$^b$ | 3.67 s | 3.70 s |
| H-17 | 3.92 s | 3.92 s | 3.92 s | 3.92 s 3.96 s$^b$ | 3.92 s 3.96 s$^b$ | 3.95 s | 3.96 s |
| H-2' | 6.86, 6.84 2 × d(1.7) | ~6.83 br | 6.82 br | 6.81, 6.85 6.86 d(1.5)$^b$ | 6.93 d(1.5) 6.85 d(1.5)$^b$ | 6.85 d(1.5) | |
| H-5' | 6.92-6.89 | 6.97, 6.91 2 × d(7.9) | n.d. | n.d. 6.99 d(8.0)$^b$ | 6.91, 6.98 6.98 d(8.0)$^b$ | 7.05 d(7.9) | 6.98 d(8.0) |
| H-6' | 6.82, 6.80 2 × d(1.7, 7.9) | 6.81, 6.79 2 × dd(1.7 7.9) | ~6.78 br | 6.78 br 6.78$^b$ | 6.77 dd (1.5; 8.0) 6.78 dd (1.5; 8.0)$^b$ | 6.80 dd 1.5; 7.9) | 6.78 dd (1.5; 8.0) |
| H-1"$^d$ | 5.34, 5.30 2 × d(8.0) | 5.35, 5.33 2 × d(8.0) | ~5.36 | 5.37 d(8.0) | 5.37 d(8.0) | | |

$^a$Spectra were recorded using DMSO-d$_6$ solutions; chemical shifts are reported in ppm relative TMS. Figures in parentheses are coupling constants in Hertz;
$^b$Signals attributed to justicidin B;
$^c$Acetic acid obtained by hydrolysis of glycoside;
$^d$Glucose protons H-2"-6" appear as broad or split signals between 4.20 and 3.05 ppm;
n.d.: not detected.

TABLE 2

High-field (400 MHz) $^1$H nmr chemical shifts for phyllanthostatin A (1a), peracetate (1b) and perpropionate (1c)$^a$.

| assignment | 1a | 1b | 1c |
|---|---|---|---|
| H-4 | 7.78 s$^b$ | 7.72 s$^b$ | 7.72 s$^b$ |
| H-5 | 7.17 s | 7.15 s | 7.14 s$^b$ |
| H-8 | 6.88 s | 6.90-6.73 | 6.92-6.72 |
| H-11 | 5.37, 5.27 5.34, 5.29 4 × d (12.5) | 5.31-5.04 m | 5.30-5.09 m |
| H-13 | 2.09 s$^b$ | 2.10-2.00$^c$ | 2.07, 2.06 2 × s |
| H-15 | 6.07-6.05 m | 6.05-6.02 m | 6.05-6.02 m |
| H-16 | 3.79 s | 3.78 s | 3.78 s |
| H-17 | 4.03 s | 4.02 s | 4.01 s |
| H-2' | 6.85, 6.83 2 × d (1.5) | 6.90-6.73 | 6.92-6.72 |
| H-5' | 6.94-6.92 | 6.90-6.73 | 6.92-6.72 |
| H-6' | 6.94-6.92 | 6.90-6.73 | 6.92-6.72 |
| H-1" | 5.58, 5.55 2 × d (8.0) | 5.75, 5.74 2 × d (8.2) | 5.75, 5.74 2 × d (8.0) |
| H-2"-6" | 3.61-3.33 | 5.31-5.04 4.20-4.04 | 5.30-5.09 4.20-4.02 |
| —COCH$_3$ | | 2.10-2.00$^c$ | |
| —COCH$_2$CH$_3$ | | | 2.40-2.23 |
| —COCH$_2$CH$_3$ | | | 1.17-1.04 |

$^a$spectra were recorded using CDCl$_3$ solutions; chemical shifts are reported in ppm relative to TMS; Figures in parentheses are coupling constants in Hertz;
$^b$signal split by ~0.005 ppm;
$^c$5 acetyl singlets split into 10 signals.

TABLE 3

The $^{13}$C nmr and heteronuclea correlation results obtained from phyllanthostatin A (1a)$^a$.

| Chemical shift$^b$ | one-bond $^1$H, $^{13}$C - correlation$^c$ | long-reange $^1$H, $^{13}$C correlation$^d$ |
|---|---|---|
| 1  137.31/137.16 (2xs) | | H-2', H-6', H-8 |
| 2  128.59/128.39 (2xs) | | H-4, H-11 |
| 3  127.70/127.60 (2xs) | | H-11 |
| 4  126.92 (d) | 7.54 | H-5, H-11 |
| 5  106.37 (d) | 7.06 | H-4 |
| 6  150.63 (s) | | H-8, H-17 |
| 7  150.35 (s) | | H-5, H-16 |
| 8  105.45/105.35 (2xd) | 6.88$^e$ | |
| 9  127.70/127.60 (2xs) | | H-4, H-5 |
| 10  129.70 (s) | | H-8 |
| 11  65.26 (t) | 5.25, 5.12 | |
| 12  172.92 (s) | | H-13 |
| 13  21.00 (q) | 1.99 | |
| 14  167.42 (s) | | H-1", H-4$^f$ |
| 15  101.28 (t) | 5.98, 5.91 | |
| 16  55.79 (q) | 3.71 | |
| 17  55.94 (q) | 4.00 | |
| 1'  131.17/131.10 (2xs) | | H-5' |
| 2'  110.84/110.56 (2xd) | 6.83$^e$ | H-6' |
| 3'  147.58-147.31 (2xs)$^i$ | | H-5', H-15 |
| 4'  147.58-147.31 (2xs)$^i$ | | H-2', H-15 |
| 5'  108.31/108.15 (2xd) | 6.90$^e$ | |
| 6'  123.86/123.71 (2xd) | 6.80$^e$ | H-2' |
| 1"  94.37 (d) | 5.52 | |
| 2"  72.43 (d)$^g$ | 3.44 | |
| 3"  76.42 (d)$^{g,h}$ | 3.38 | |
| 4"  69.20 (d)$^g$ | 3.54 | |
| 5"  76.32 (d)$^{g,h}$ | 3.58 | |
| 6"  61.34 (d)$^g$ | 3.73 | |

$^a$50 mg (200 mg for COLOC) sample in CDCl$_3$;
$^b$in ppm downfield to TMS; multiplicities determined by APT experiments;
$^c$one-bond correlations observed in the 1$_H$ 13$_C$-COSY spectrum;
$^d$long-range couplings through two, three and four bonds observed in a $^1$H, $^{13}$C-COLOC experiment optimized for J$_{CH}$ = 5 Hz;
$^e$correlation peak doubled;
$^f$correlation peak of low intensity;
$^g$signals split by ≦0.08 ppm;
$^h$assignment may be reversed; and
$^i$overlapping signals.

EXAMPLE IV

Hydrolysis of Phyllanthostatin A

A solution of glycoside (50 mg) in CH$_3$OH (5 ml) and HCl (25 ml) was heated at reflux for 30 min, diluted with H$_2$O and extracted with CHCl$_3$. The chlorocarbon phase was washed with water and solvent evaporated to dryness. The residue was recrystallized from CH$_3$OH to afford pure justicidin B, mp 244°–247° C. (lit. (3) mp 263°–265° C. from CH₂Cl₂-CH₃OH identical (by ir and ¹H-nmr) with an authentic specimen. The aqueous phase was neutralized (NaHCO₃), solvent evaporated, and the glucose extracted with pyridine. Glucose was detected in the extract by tlc on silica gel using the solvent system AcOEt-CH₃OH-H₂O-HOAc (65:15:15:30) followed by spraying with anisaldehyde reagent and heating to reveal a greyish green spot (Rf=0.61) characteristic of D-glucose. The pyridine solution was treated with acetic anhydride (room temp., 24 hours). The product was purified by silica gel column chromatography in CH₂Cl₂CH₃OH (95:5) and 8 mg of glucose pentaacetate was obtained. Identical ¹H-nmr chemical shifts and eims spectra were observed with an authentic sample of D-glucose pentaacetate, prepared under the same conditions.

EXAMPLE V

Phyllanthostatin A Peracetate

Glycoside (5 mg) was acetylated in pyridine-acetic anhydride and the product purified by silica gel column chromatography with CH₂Cl₂-MeOH (98:2) as eluent to yield the peracetate as an amorphous solid (4 mg): tlc on silica gel, Rf=0.24, n-hexane-AcOEt (1:1), hrfabms, m/z 761.2228 [M+Li]⁺ (calculated for C₃₇H₃₈O₁₇Li: 761.2270, Δ=5.5 ppm), 371 [(M+Li)-390]⁺, 365 (M+H)-390]⁺; ir νmax 2860, 1758, 1506, 1493, 1434, 1370, 1237, (br), 1156, 1059, 1039; and for the ¹H nmr see Table 2, supra.

EXAMPLE VI

Phyllanthostatin A Perpropionate

A solution of glycoside (4mg) in pyridine (0.2 ml) and propionic anhydride (0.2 ml) was stored at room temp. After two days solvent was evaporated (under N₂) while CH₃OH was repeatedly added. The residue was chomatographed as noted above for obtaining peracetate to afford 3.5 mg of perpropionate as an amorphous solid; tlc on silica gel, Rf=0.59, n-hexane-AcOEt (1:2); hrfabms m/z 810.2734 [M]⁺ (calculated for C₄₁H₄₆O₁₇: 810.2721, Δ=1.6 ppm), 752 [(M+H)-59]⁺, 424.1172 [M-386]⁺ (calculated for C₂₃H₂₀O₈: 424.1152 Δ=4.7 ppm), 387 (glucose tetrapropionate), 365 [(M+H)-446]⁺. The ¹H nmr data appears in Table 2, supra.

EXAMPLE VII

Phyllanthostatin A was tested using the United States National Cancer Institute standard protocol for P388 murine lymphocytic leukemia (in vitro PS system) and produced ED₅₀ =4 μug/ml.

From the foregoing it is readily apparent that a novel lignan glycoside has been herein described and illustrated which fulfills all of the aforestated objectives in a remarkably unexpected fashion It is of course understood that such modifications, alterations and adaptations as may readily occur to the artisian confronted with this disclosure are intended within the spirit of the present invention which is limited solely by the scope of the claims appended hereto.

Accordingly, what is claimed is:

1. A lignan glycoside derived from *P. acuminatus* and having the structural formula:

[Structural formula of lignan glycoside with numbered carbons: CH₃O groups at positions 16, 17; naphthalene ring system with positions 1-10; ester linkages at positions 11-13 and 14-15; phenyl group with positions 1'-6'; sugar moiety with positions 1"-6" bearing OH groups]

2. A lignan glycoside which, when placed as a 50 mg sample in CDCL₃, provides the following ¹³C nmr and heteronuclear correlation results:

| Chemical shift[b] | one-bond ¹H, ¹³C-correlation[c] | long-range ¹H, ¹³C correlation[d] |
|---|---|---|
| 1 137.31/137.16 (2xs) | | H-2', H-6', H-8 |
| 2 128.59/128.39 (2xs) | | H-4, H-11 |
| 3 127.70/127.60 (2xs) | | H-11 |
| 4 126.92 (d) | 7.54 | H-5, H-11 |
| 5 106.37 (d) | 7.06 | H-4 |
| 6 150.63 (s) | | H-8, H-17 |
| 7 150.35 (s) | | H-5, H-16 |
| 8 105.45/105.35 (2xd) | 6.88[e] | |
| 9 127.70/127.60 (2xs) | | H-4, H-5 |
| 10 129.70 (s) | | H-8 |
| 11 65.26 (t) | 5.25, 5.12 | |
| 12 172.92 (s) | | H-13 |
| 13 21.00 (q) | 1.99 | |
| 14 167.42 (s) | | H-1', H-4[f] |
| 15 101.28 (t) | 5.98, 5.91 | |
| 16 55.79 (q) | 3.71 | |
| 17 55.94 (q) | 4.00 | |
| 1' 131.17/131.10 (2xs) | | H-5' |
| 2' 110.84/110.56 (2Xd) | 6.83[e] | H-6' |
| 3' 147.58-147.31 (2xs)[i] | H-5', H-15 | |
| 4' 147.58-147.31 (2xs)[i] | | H-2', H-15 |
| 5' 108.31/108.15 (2xd) | 6.90[e] | |
| 6' 123.86/123.71 (2xd) | 6.80[e] | H-2' |
| 1" 94.37 (d) | 5.52 | |
| 2" 72.43 (d)[g] | 3.44 | |
| 3" 76.42 (d)[g,h] | 3.38 | |
| 4" 69.20 (d)[g] | 3.54 | |
| 5| 76.32 (d)[g,h] | 3.58 | |
| 6" 61.34 (d)[g] | 3.73 | |

[b]in ppm downfield to TMS; multiplicities by APT experiments;
[c]one-bond correlations observed in the 1_H 13_C-COSY spectrum;
[d]long-range couplings through two, three and four bonds observed in a ¹H, ¹³C-COLOC experiment optimized for $J_{CH}$ = 5 Hz;
[e]correlation peak doubled;
[f]correlation peak of low intensity;
[g]signals split by ≦0.08 ppm;
[h]assignment may be reversed; and
[i]overlapping signals.

3. A method of inhibiting cell growth in NCI P388 murine lymphocytic leukemia comprising treating said leukemia with a cell growth inhibiting amount of phyllanthostatin A.

4. A method of inhibiting cell growth in a host afflicted with a neoplastic disease correlatable to P388 murine lymphocytic leukemia comprising administering to said host a cell growth inhibiting amount of phyllanthostatin A.

* * * * *